US006379935B1

(12) United States Patent
Kamachi et al.

(10) Patent No.: US 6,379,935 B1
(45) Date of Patent: Apr. 30, 2002

(54) METHOD OF PRODUCING α-HALO-α, β-SATURATED CARBONYL COMPOUNDS FROM THE CORRESPONDING α,β-UNSATURATED COMPOUNDS

(75) Inventors: Harumi Kamachi; Tadashi Yoneda; Motoaki Kamachi, all of Chiba; Nobuyoshi Esaki, Shiga, all of (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/369,144

(22) Filed: Aug. 5, 1999

Related U.S. Application Data
(60) Provisional application No. 60/138,085, filed on Jun. 8, 1999.

(30) Foreign Application Priority Data

Aug. 7, 1998 (JP) ............................................ 10-224821

(51) Int. Cl.$^7$ ............................. C12P 17/10; C12P 1/00; C12P 17/02; C12P 11/00; C12P 7/00
(52) U.S. Cl. ......................... 435/121; 435/41; 435/123; 435/130; 435/132; 435/135; 435/136
(58) Field of Search .................................. 435/280, 106, 435/117, 128, 130, 132, 41, 121, 123, 135, 136

(56) References Cited

FOREIGN PATENT DOCUMENTS

JP        11-196889        7/1999

OTHER PUBLICATIONS

R. Eck, et al, "Preparation of (S)–2–substituted succinates by stereospecific reductions of fumarate and derivatives with resting cells of *Clostridium formicoaceticum*," *Tetrahedron*, (1994), 50(48), 13631–13640.

Markus Christen, et al, "Biotransformations Using Clostridia: Stereospecific Reductopm of a β–Keto Ester", *J. Chem. Soc., Perkin Trans. 1*, (1992), (4), pp. 491–493.

Yasushi Kawai, et al., "Asymmetric Reduction of α,β–Unsaturated Ketones with a Carbon–Carbon Double–Bon Reductase from Baker's Yeast," *Tetrahedron Lett.*, (1998), 39(29), pp. 5225–5228.

Lugwig Angermaier, et al., "Stereospecific Reductions of 2–En–1–ols Catalyzed by *Clostridium kluyverk*", *Hoppe-–Seyler's Z. Physiol. Chem.*, (1981), 362(1), pp. 33–38.

Hermine Giesel and Helmet Simon, "On The Occurence Of Enoate Reductase 2–oxo–Carboxylate Reductase In Clostridia And Some Observations On The Amino Acid Fermentation by *Peptostreptococcus Anaerobius*," *Arch. Microbiol.*, (1983), 135(1), pp. 51–57.

*Primary Examiner*—Sandra E. Saucier
(74) *Attorney, Agent, or Firm*—Sughrue Mion, PLLC

(57) ABSTRACT

A method of producing an α-halo-α,β-saturated carbonyl compound from an α-halocarbonyl compound having an α, β-carbon-carbon double bond by reducing said α,β-carbon-carbon double bond using a microorganism belonging to any one of the genera Acetobacter, Actinomyces, Acinetobacter, Agrobacterium, Aeromonas, Alcaligenes, Arthrobacter, Azotobacter, Bacillus, Brevibacterium, Burkholderia, Cellulomonas, Corynebacterium, Enterobacter, Enterococcus, Escherichia, Flavobacterium, Gluconobacter, Halobacteium, Halococccus, Klebsiella, Lactobacillus, Microbacterium, Micrococcus, Micropolyspora, Mycobacterium, Nocardia, Pseudomonas, Pseudonocardia, Rhodococcus, Rhodobacter, Serratia, Staphylococcus, Streptococcus and Streptomyces, Xanthomonas, or a microbial product thereof. Pseudomonas sp. SD810, SD811 and SD812, Burkholderia sp. SD 816, and mutants thereof having an activity of reducing the α,β-carbon-carbon double bond of an a-halocarbonyl compound having an α, β-carbon-carbon double bond.

17 Claims, 2 Drawing Sheets

METHOD OF PRODUCING α-HALO-α,β-SATURATED CARBONYL COMPOUNDS FROM THE CORRESPONDING α,β-UNSATURATED COMPOUNDS

CROSS REFERENCE TO RELATED APPLICATIONS

This application is an application filed under 35 U.S.C. §111(a) claiming benefit pursuant to 35 U.S.C. §119(e)(i) of the filing date of the Provisional Application 60/138,085 filed Jun. 8, 1999 pursuant to 35 U.S.C. §111(b).

FIELD OF THE INVENTION

The present invention relates to a method of producing a corresponding α-halo-α,β-saturated carbonyl compound from an α-halocarbonyl compound having an α,β-carbon-carbon double bond by hydrogenating the α,β-carbon-carbon double bond using a microorganism belonging to the genus Acetobacter, Actinomyces, Acinetobacter, Agrobacterium, Aeromonas, Alcaligenes, Arthrobacter, Azotobacter, Bacillus, Brevibacterium, Burkholderia, Cellulomonas, Corynebacterium, Enterobacter, Enterococcus, Escherichia, Flavobacterium, Gluconobacter, Halobacteium, Halococccus, Klebsiella, Lactobacillus, Microbacterium, Micrococcus, Micropolyspora, Mycobacterium, Nocardia, Pseudomonas, Pseudonocardia, Rhodococcus, Rhodobacter, Serratia, Staphylococcus, Streptococcus, Streptomyces or Xanthomonas, preferably a microorganism belonging to the genus Pseudomonas or Burkholderia, more preferably Pseudomonas sp. SD810, Pseudomonas sp. SD811, Pseudomonas sp. SD812 or Burkholderia sp. SD816, or a microbial product thereof. The present invention also relates to novel microorganisms belonging to the genera Pseudomonas and Burkholderia, particularly Pseudomonas sp. SD810, Pseudomonas sp. SD811, Pseudomonas sp. SD812 and Burkholderia sp. SD816.

Furthermore, the present invention relates to a method of producing a corresponding α-halo-α,β-saturated carbonyl compound as an S form compound with respect to the α-position from an α-halocarbonyl compound having an α,β-carbon-carbon double bond by hydrogenating the carbon-carbon double bond. This method can be used in the production of optically active carbonyl compounds such as various optically active (having an absolute S form configuration at the α-position) saturated carboxylic acids or amides. The optically active carbonyl compounds are a highly valuable chiral building block which is difficult to prepare by classical chemical processes, and are materials useful particularly as a raw material of medical or agricultural chemicals.

BACKGROUND OF THE INVENTION

In recent years, a method of producing various compounds, particularly optically active substances, by the reduction of a carbon-carbon double bond using a microorganism is drawing attention. To this effect, various methods of producing a corresponding α,β-saturated carbonyl compound having a substituent at the α-position from a carbonyl compound having an α,β-carbon-carbon double bond and having a substituent at the α-position by microbially reducing the carbon-carbon double bond have been reported (see, H. Simon, et al., *Hoppe-Seyler's Z. Physiol. Chem.*, 362, 33 (1981), H. Giesel, et al., *Arch. Microbiol.*, 135, 51 (1983), H. G. W. Leuenberger, et al., *Helv. Chim. Acta.*, 62, 455 (1979), R. Matsuno, et al., *J. Ferm. Bioeng.*, 84, 195 (1997)).

However, for example, according to the method of using bacteria as the microorganism, an anaerobe such as *Clostridium kluyveri* (DSM-555) or Clostridium sp. La-1 (DSM-1460) is used. Therefore, the growing rate of the microorganism is slow, it is difficult to increase the cell concentration and accordingly, the reaction rate is not satisfactorily high. Thus, these methods have a problem in profitability and operability.

The method using *Clostridium theremosaccharolyticum* disclosed in JP-A-63-003794 (the term "JP-A" as used herein means an "unexamined published Japanese patent application") has an object of solving the above-described problem by using a thermophilic bacterium. However, the bacterium used is still anaerobic, therefore, the growing rate and the reaction rate both are not satisfactorily high and the process involves use of hydrogen. Thus, the method fails in solving the problems in profitability and safety. Furthermore, the α,β-saturated carbonyl compound having a substituent at the α-position produced by reducing a prochiral carbonyl compound having an α,β-carbon-carbon double bond and having a substituent at the α-position using a microorganism is a compound having an absolute R form configuration and an S form configuration compound cannot be produced.

The method of reducing the α,β-carbon-carbon double bond using a bread yeast as the microorganism has general-purpose applicability because compounds over a wide range can be reduced. In addition, since the microorganism used is aerobic, good operability can be attained. Furthermore, the optically active substances produced include both S form and R form, therefore, this method is most abundant in the cases reported. However, the yeast grows slowly as compared with bacteria, the optical selectivity is not sufficiently high in many cases in the reduction reaction for obtaining a more optically active product, and reduction of an α-halocarbonyl compound having an α,β-carbon-carbon double bond is not known.

As described above, in the technique of producing a corresponding α-halo-α,β-saturated carbonyl compound from an α-halocarbonyl compound having an α,β-carbon-carbon double bond by reducing the carbon-carbon double bond using a microorganism, a method satisfying all of the requirements regarding operability, profitability, safety and reaction properties is not yet known.

SUMMARY OF THE INVENTION

An object of the present invention is to provide a method of producing a corresponding α-halo-α,β-saturated carbonyl compound from an α-halocarbonyl compound having an α,β-carbon-carbon double bond by reducing the carbon-carbon double bond using a microorganism, which method can satisfy all of the requirements for operability, profitability, safety and reaction properties and ensure excellent optical selectivity.

As a result of thorough screening from soil, the present inventors have found that surprisingly, microorganisms capable of producing a corresponding α-halo-α,β-saturated carbonyl compound from an α-halocarbonyl compound having an α,β-carbon-carbon double bond by reducing the carbon-carbon double bond are distributed over a relatively wide genus range of the aerobes and facultative anaerobes. In particular, it has been found that strains having this activity are present in a large number in microorganisms belonging to the genera Pseudomonas and Burkholderia, and some of these strains can reduce an α-halocarbonyl compound having an α,β-carbon-carbon double bond and thereby produce an extremely high-purity α-halo-α,β-saturated carbonyl compound having an absolute configuration of S form at the α-position. The present invention has been accomplished based on these findings.

More specifically, the present invention relates to the following embodiments:

[1] a method of producing an α-halo-α,β-saturated carbonyl compound from an α-halocarbonyl compound having an α,β-carbon-carbon double bond by reducing the α,β-carbon-carbon double bond using a microorganism belonging to any one of the genera Acetobacter, Actinomyces, Acinetobacter, Agrobacterium, Aeromonas, Alcaligenes, Arthrobacter, Azotobacter, Bacillus, Brevibacterium, Burkholderia, Cellulomonas, Corynebacterium, Enterobacter, Enterococcus, Escherichia, Flavobacterium, Gluconobacter, Halobacteium, Halococcus, Klebsiella, Lactobacillus, Microbacterium, Micrococcus, Micropolyspora, Mycobacterium, Nocardia, Pseudomonas, Pseudonocardia, Rhodococcus, Rhodobacter, Serratia, Staphylococcus, Streptococcus, Streptomyces and Xanthomonas, or a microbial product thereof;

[2] the method of producing an α-halo-α,β-saturated carbonyl compound as described in [1], wherein the α,β-carbon-carbon double bond of the α-halocarbonyl compound having an α,β-carbon-carbon double bond is reduced using a microorganism belonging to the genus Pseudomonas or a microbial product thereof;

[3] the method of producing an α-halo-α,β-saturated carbonyl compound as described in [1], wherein the α,β-carbon-carbon double bond of the α-halocarbonyl compound having an α,β-carbon-carbon double bond is reduced using a microorganism belonging to the genus Burkholderia or a microbial product thereof;

[4] the method of producing an α-halo-α,β-saturated carbonyl compound as described in [2], wherein the microorganism belonging to the genus Pseudomonas is Pseudomonas sp. SD810;

[5] the method of producing an α-halo-α,β-saturated carbonyl compound as described in [2], wherein the microorganism belonging to the genus Pseudomonas is Pseudomonas sp. SD811;

[6] the method of producing an α-halo-α,β-saturated carbonyl compound as described in [2], wherein the microorganism belonging to the genus Pseudomonas is Pseudomonas sp. SD812;

[7] the method of producing an α-halo-α,β-saturated carbonyl compound as described in [3], wherein the microorganism belonging to the genus Burkholderia is Burkholderia sp. SD816;

[8] the method of producing an α-halo-α,β-saturated carbonyl compound as described in [1] to [7], wherein an S-form compound chiral at the α-position is produced by the reduction of the carbon-carbon double bond;

[9] the method of producing an α-halo-α,β-saturated carbonyl compound as described in [1] to [8], wherein the α-halocarbonyl compound having an α,β-carbon-carbon double bond is a compound represented by the following formula (1):

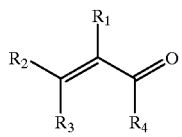

wherein $R_1$ represents a halogen atom, $R_2$ and $R_3$ each independently represents a hydrogen atom, a halogen atom, a linear or branched aliphatic hydrocarbon group having from 1 to 6 carbon atoms, a linear or branched alkoxy group having from 1 to 6 carbon atoms, a hydroxyl group, a carboxyl group, an aromatic group which may be substituted, or a nitrogen-, oxygen- or sulfur-containing heterocyclic group, and $R_4$ represents a hydroxyl group, a linear or branched alkoxy group having from 1 to 3 carbon atoms or a primary, secondary or tertiary amino group) and the α-halo-α,β-saturated carbonyl compound is a compound represented by the following formula (2):

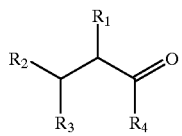

wherein $R_1$ to $R^4$ have the same meanings as defined above;

[10] the method of producing an α-halo-α,β-saturated carbonyl compound as described in [9], wherein the compound represented by formula (1) is an α-haloacrylic acid and the compound represented by formula (2) is an α-halopropionic acid having an absolute S form configuration;

[11] the method of producing an α-halo-α,β-saturated carbonyl compound as described in [10], wherein the halogen atom is a bromine atom;

[12] the method of producing an α-halo-α,β-saturated carbonyl compound as described in [10], wherein the halogen atom is a chlorine atom;

[13] the method of producing an α-halo-α,β-saturated carbonyl compound as described in [1] to [12], wherein the microbial product of a microorganism is a microorganism culture, a microbial extract, a microbial cell suspension or a microbial cell fixed to a support;

[14] the method of producing an α-halo-α,β-saturated carbonyl compound as described in [1] to [13], wherein the microorganism used is varied not to decompose the α-halo-α,β-saturated carbonyl compound produced, thereby increasing the amount of the product accumulated;

[15] the method of producing an α-halo-α,β-saturated carbonyl compound as described in [1] to [14], wherein the α-halocarbonyl compound having an α,β-carbon-carbon double bond and a compound capable of being oxidized by the microorganism used are present together in the reaction system and thereby the reaction continuing time is prolonged;

[16] the method of producing an α-halo-α,β-saturated carbonyl compound as described in [15], wherein the compound capable of being oxidized by the microorganism used is a sugar having from 3 to 6 carbon atoms;

[17] the method of producing an α-halo-α,β-saturated carbonyl compound as described in [15], wherein the compound capable of being oxidized by the microorganism used is an organic acid having from 2 to 4 carbon atoms;

[18] Pseudomonas sp. SD810 and mutants thereof having an activity of reducing the α,β-carbon-carbon double bond of an α-halocarbonyl compound having an α,β-carbon-carbon double bond;

[19] Pseudomonas sp. SD811 and mutants thereof having an activity of reducing the α,β-carbon-carbon double bond of an α-halocarbonyl compound having an α,β-carbon-carbon double bond;

[20] Pseudomonas sp. SD812 and mutants thereof having an activity of reducing the α,β-carbon-carbon double bond of an α-halocarbonyl compound having an α,β-carbon-carbon double bond;

[21] Burkholderia sp. SD816 and mutants thereof having an activity of reducing the α,β-carbon-carbon double bond of an α-halocarbonyl compound having an α,β-carbon-carbon double bond;

[22] a microbial product containing the microorganism described in [12] to [21]; and

[23] the microbial product as described in [22], which is a microbial culture, a microbial extract, a microbial cell suspension or a microbial cell fixed to a support.

DESCRIPTION OF THE PREFERRED EMBODIMENTS

Figure 1:
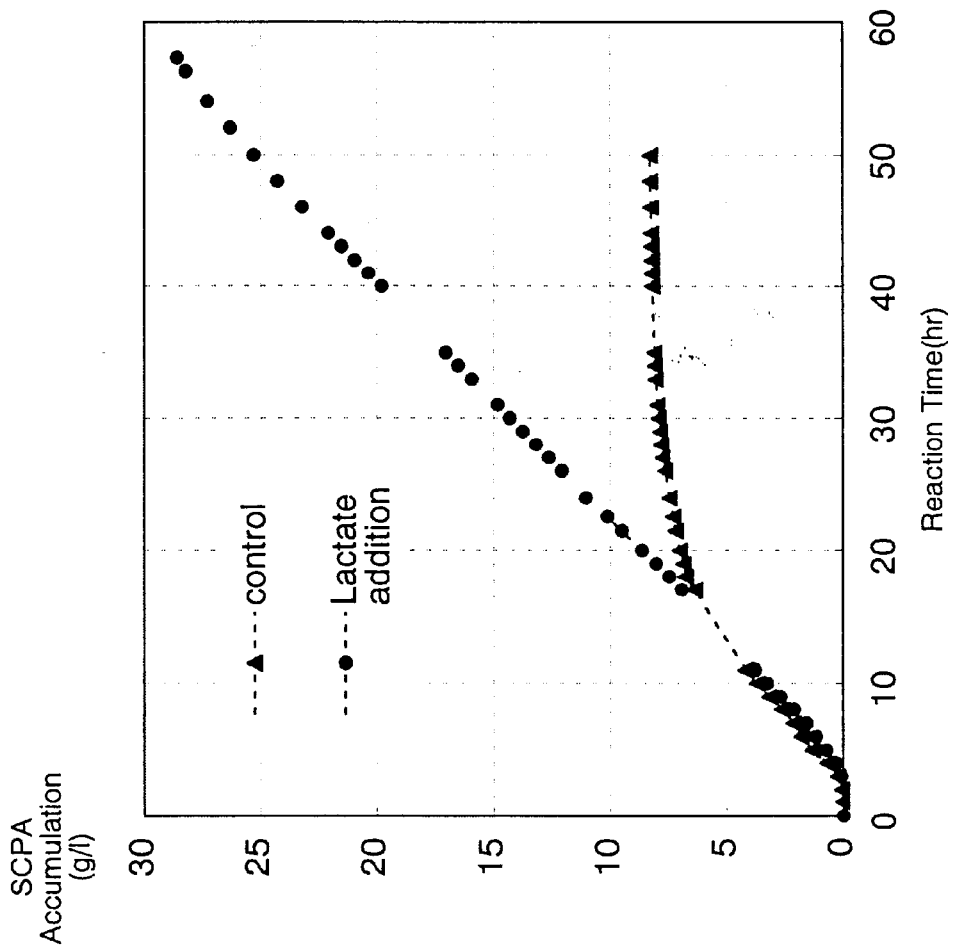
FIG. 1 shows an example of the accumulative production of α-chloropropionic acid in the cases where a substance to be oxidized is not present and where such is present.
Figure 2:
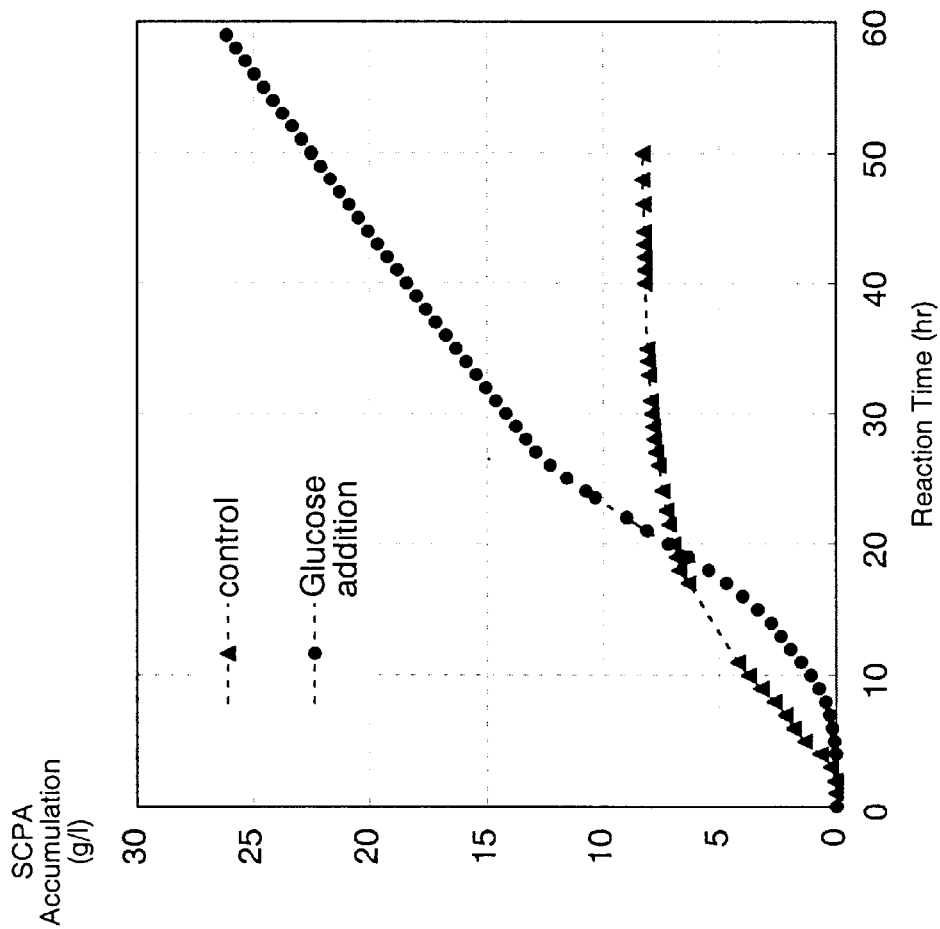
FIG. 2 shows an example of the accumulative production of α-chloropropionic acid in the cases where glucose is not present and where such is present.

The microorganisms which can be used in the present invention are microorganisms belonging to any one of the genera Acetobacter, Actinomyces, Acinetobacter, Agrobacterium, Aeromonas, Alcaligenes, Arthrobacter, Azotobacter, Bacillus, Brevibacterium, Burkholderia, Cellulomonas, Corynebacterium, Enterobacter, Enterococcus, Escherichia, Flavobacterium, Gluconobacter, Halobacteium, Halococccus, Klebsiella, Lactobacillus, Microbacterium, Micrococcus, Micropolyspora, Mycobacterium, Nocardia, Pseudomonas, Pseudonocardia, Rhodococcus, Rhodobacter, Serratia, Staphylococcus, Streptococcus, Streptomyces and Xanthomonas.

Among these, microorganisms belonging to the genera Pseudomonas and Burkholderia are preferred. The strain is not particularly limited as long as it has an activity of reducing the α,β-carbon-carbon double bond of an α-halocarbonyl compound having an α,β-carbon-carbon double bond. However, for example, Pseudomonas sp. SD810, Pseudomonas sp. SD811, Pseudomonas sp. SD812 and Burkholderia sp. SD816 are preferably used. Among these, Pseudomonas sp. SD811 and Burkholderia sp. SP816 are more preferred. The strains Pseudomonas sp. SD810, Pseudomonas sp. SD811, Pseudomonas sp. SD812 and Burkholderia sp. SD816 of Bioscience and Human-Technology at 1–3, Higashi 1 chome Tsukuba-shi Ibaraki-ken 305-8566, JAPAN under the accession numbers Pseudomonas sp. SD810: BP-6767 (FERM BP-6767) (transferred from accession number 16746 (FERM-16746)), Pseudomonas sp. SD811: BP-6768 (FERM BP-6768) (transferred from accession number 16747 (FERM-16747)) and Pseudomonas sp. SD812: BP-6769 (FERM BP-6769) (transferred from accession number 16748 (FERM-16748)), respectively. All deposited specimens described in this application were deposited on Jun. 28, 1999.

The above-described microorganisms may be any of a wild type, variant and recombinant induced by cell fusion or genetic engineering as long as the strain has an activity of reducing the carbon-carbon double bond of an α-halocarbonyl compound having an α,β-carbon-carbon double bond. For example, a variant reduced or defective in activity of decomposing the product, a variant or recombinant improved in reducing activity or a variant improved in resistance against a high-concentration substrate or product may be preferably used.

Examples of the isolation and cultivation of these strains are described below.

5 ml of a minimum medium obtained by adding, as a substantially sole carbon source, 2 g/l of an α,β-unsaturated carbonyl compound having a halogen atom as a substituent at the α-position, such as α-chloroacrylic acid, to an inorganic salt culture medium (for example, $(NH_4)_2SO_4$: 2 g/l, $NaH_2PO_4$: 1 g/l, $K_2HPO_4$: 1 g/l, $MgSO_4$: 0.1 g/l, yeast extract: 0.5 g/l) used for normal bacteria is poured in a test tube and sterilized. Thereafter, about 0.1 g of soil is added thereto and cultivation by shaking is performed at 28° C. Subculture is performed every single day. After repeating this accumulative cultivation for 6 days, the culture is spread on the agar plate of minimum medium described above containing 20 g/l of agar as a solidifying agent, and cultured at 28° C. for 3 days. By the isolation of colonies produced, the strain Pseudomonas sp. SD810, Pseudomonas sp. SD811 or Pseudomonas sp. SD812 may be obtained. These strains Pseudomonas sp. SD810, Pseudomonas sp. SD811 and Pseudomonas sp. SD812 are deposited with National Institute of Bioscience and Human-Technology under the accession numbers BP-6767 (FERM BP-6767) (transferred from accession number 16746 (FERM-16746)), BP-6768 (FERM BP-6768) (transferred from accession number 16747 (FERM-16747)) and BP-6769 (FERM BP-6769) (transferred from accession number 16748 (FERM-16748)), respectively.

Examples of the isolation and cultivation of the strains having a relatively small population in isolation source are described below.

By accumulative acclimatization using soil as the separation source, microorganisms having a small population, microorganisms having a low assimilating activity or microorganisms having a low resistance against α, β-unsaturated carbonyl compounds having a halogen atom as the substituent at the α-position (hereinafter sometimes referred to as a "halogen-containing compound"), such as α-chloroacrylic acid, may be separated. More specifically, 0.01% (in the present specification, unless otherwise indicated, "%" is "weight (g)/volume (100 ml)×100") of various halogen-containing compounds are added as a substantially sole carbon source or added together with glucose in the same concentration to a basal medium containing yeast extract (0.5 g/l), ammonium sulfate (2 g/l), sodium dihydrogenphosphate (1 g/l), dipotassium hyrogenphosphate (1 g/l) and magnesium sulfate (0.1 g/l) (for the isolation of some microorganisms which require a high salt concentration to grow, a medium obtained by adding sodium chloride in a concentration of from 10 to 20% to the above-described basal medium is used as the basal medium). In 10 ml of the thus-prepared medium, 1 g of soil collected is suspended and cultured by shaking at 30° C. After 24 hours, 5 ml of the supernatant of the culture is sampled and after adding thereto 5 ml of a new medium having the same composition as above except that the concentration of halogen-containing compounds is 0.02%, cultured by shaking at 30° C. (first subculture). After 24 hours, 5 ml of the supernatant of the culture was sampled and after adding thereto 5 ml of the medium where the concentration of halogen-containing compounds in the medium is increased from 0.02% to 0.1%, cultured by shaking at 30° C. (second subculture). This operation is further repeated 3 times every 24 hours (third to fifth subculture). At the sixth subculture, the concentration of halogen-containing compounds in the medium added to the culture is increased to 0.2% and 5 ml of the supernatant is sampled and after adding thereto 5 ml of a new medium, cultured by shaking at 30° C. 1S This operation is repeated 6 times (sixth to twelfth subculture) every 24 hours. At each time of these 6 subculture operations, a part of the supernatant of the culture is spread on a agar plate obtained by adding 2% of agar to the above-described medium containing 0.2% of halogen containing compounds, and cultured at 30° C. The colonies produced are pure separated and then, for example, Burkholderia sp. SD816 may be obtained. Burkholderia sp. SD816 is deposited with National Institute of Bioscience and Human-Technology under the accession number BP-6770 (FERM BP-6770).

The taxonomic test results of these strains are shown below.

Pseudomonas sp. SD810

Morphology

| | | |
|---|---|---|
| (1) | Shape and size of cell | rod |
| | 0.6–1.0 μm × 1.2–3.0 μm | |
| (2) | Motility | motile |
| (3) | Gram staining | negative |
| (4) | Spore | none |
| (5) | Bacteriolysis by 3% KOH | positive |

Physiological activity:

| | | |
|---|---|---|
| (1) | Aminopeptidase | positive |
| (2) | Oxidase | positive |
| (3) | Catalase | positive |
| (4) | Production of indole | negative |
| (5) | VP test | negative |
| (6) | Reduction of nitrate | negative |
| (7) | Denitrification | negative |
| (8) | Use of citric acid (Simons) | positive |
| (9) | Urease | negative |
| (10) | Phenylalanine deaminase | negative |
| (11) | Use of maronic acid | positive |
| (12) | Production of levan from sucrose | positive |
| (13) | Lecithinase | negative |
| (14) | Hydrolysis of starch | negative |
| (15) | Hydrolysis of gelatin | negative |
| (16) | Hydrolysis of casein | negative |
| (17) | Hydrolysis of DNA | negative |
| (18) | Hydrolysis of Tween 80 | negative |
| (19) | Hydrolysis of exrin | negative |
| (20) | Growth | – |
| | Behavior to oxygen | obligately aerobic |
| | Growth at 37° C. | – |
| | Growth at 41° C. | + |
| | Growth at pH 5.6 | + |
| | Growth in Mac-Conkey-Agar medium | – |
| | Growth in SS-Agar medium | – |
| | Growth in Cetrimid-Agar | – |
| (21) | Production of dye | |
| | Nondiffusive | negative |
| | Diffusive | negative |
| | Fluorescent | negative |
| | Pyrocyanine | negative |
| (22) | OF Test | no decomposition of sugar |
| (23) | Formation of acids | |
| | Glucose | negative |
| | Fructose | positive |
| | Xylose | negative |
| (24) | ONPG (β-Galactosidase) | negative |
| (25) | Arginine dihydrolase | negative |
| (26) | Production of gas from glucose | negative |
| (27) | Tyrosine decomposition | negative |
| (28) | Growth factor request | none |
| (29) | Use of various carbon compounds | |
| | Acetic acid | + |
| | Adipic acid | – |
| | Capric acid | + |
| | Citric acid | + |
| | Citraconic acid | + |
| | Glycolic acid | + |
| | Levulinic acid | + |
| | Maleic acid | + |
| | Malonic acid | + |
| | Mesaconic acid | + |
| | Muconic acid | + |
| | Phenylacetic acid | + |
| | Saccharic acid | + |
| | Sebacic acid | + |
| | D-Tartaric acid | + |
| | m-Tartaric acid | + |
| | L-Arabinose | – |
| | Cellobiose | – |
| | Fructose | + |
| | D-Fucose | – |
| | Glucose | – |
| | Mannose | – |
| | Maltose | – |
| | Ribose | – |
| | Rhamnose | – |
| | Xylose | – |
| | Mannitol | – |
| | Gluconic acid | – |
| | 2-Ketogluconic acid | + |
| | N-Acetylglucosamine | – |
| | Tryptamine | – |
| | Ethanolamine | – |
| | D-Alanine | + |
| | L-Ornithine | – |
| | L-Serine | – |
| | L-Threonine | – |
| | Glutamic acid | + |
| | Benzoic acid | + |
| | m-Hydroxybenzoic acid | – |
| | Sodium salicinate | – |
| | 2,3-Butylene glycol | – |

When these results were taxonomically examined based on *Bergey's Manual of Systematic Bacteriology* (1986), it was found that this strain belongs to the genus Pseudomonas but the properties therof did not coincide with those of standard strains. Therefore, this strain was named Pseudomonas sp. SD810

Pseudomonas sp. SD811

Morphology

| | | |
|---|---|---|
| (1) | Shape and size of cell | rod |
| | | 0.7–0.9 μm × 1.5–3.0 μm |
| (2) | Motility | motile |
| (3) | Gram staining | negative |
| (4) | Spore | none |
| (5) | Bacteriolysis by 3% KOH | positive |

Physiological activity:

| | | |
|---|---|---|
| (1) | Aminopeptidase | positive |
| (2) | Oxidase | positive |
| (3) | Catalase | positive |
| (4) | Production of indole | negative |
| (5) | VP test | negative |
| (6) | Reduction of nitrate | negative |
| (7) | Denitrification | negative |
| (8) | Use of citric acid (Simons) | positive |

-continued

| | | |
|---|---|---|
| (9) | Urease | negative |
| (10) | Phenylalanine deaminase | negative |
| (11) | Use of malonic acid | positive |
| (12) | Production of levan from sucrose | negative |
| (13) | Lecithinase | negative |
| (14) | Hydrolysis of starch | negative |
| (15) | Hydrolysis of gelatin | negative |
| (16) | Hydrolysis of casein | negative |
| (17) | Hydrolysis of DNA | negative |
| (18) | Hydrolysis of Tween 80 | positive |
| (19) | Hydrolysis of exrin | negative |
| (20) | Growth | |
| | Behavior to oxygen | obligately aerobic |
| | Growth at 37° C. | – |
| | Growth at 41° C. | – |
| | Growth at pH 5.6 | + |
| | Growth in Mac-Conkey-Agar medium | – |
| | Growth in SS-Agar medium | – |
| | Growth in Cetrimid-Agar | – |
| (21) | Production of dye | |
| | Nondiffusive | negative |
| | Diffusive | negative |
| | Fluorescent | negative |
| | Pyrocyanine | negative |
| (22) | OF Test | no decomposition of sugar |
| (23) | Formation of acids | |
| | Glucose | positive |
| | Fructose | positive |
| | Xylose | positive |
| (24) | ONPG (β-galactosidase) | negative |
| (25) | Arginine dihydrolase | negative |
| (26) | Production of gas from glucose | negative |
| (27) | Tyrosine decomposition | negative |
| (28) | Growth factor request | none |
| (29) | Use of various carbon compounds | |
| | Acetic acid | + |
| | Adipic acid | – |
| | Capric acid | – |
| | Citric acid | – |
| | Citraconic acid | + |
| | Glycolic acid | + |
| | Levulinic acid | – |
| | Maleic acid | + |
| | Malonic acid | + |
| | Mesaconic acid | – |
| | Muconic acid | + |
| | Phenylacetic acid | + |
| | Saccharic acid | + |
| | Sebacic acid | – |
| | D-Tartaric acid | + |
| | m-Tartaric acid | – |
| | L-Arabinose | + |
| | Cellobiose | – |
| | Fructose | + |
| | D-Fucose | + |
| | Glucose | + |
| | Mannose | – |
| | Maltose | – |
| | Ribose | + |
| | Rhamnose | + |
| | Xylose | – |
| | Mannitol | + |
| | Gluconic acid | – |
| | 2-Ketogluconic acid | + |
| | N-Acetylglucosamine | + |
| | Tryptamine | – |
| | Ethanolamine | – |
| | D-Alanine | – |
| | L-Ornithine | – |
| | L-Serine | – |
| | L-Threonine | – |
| | Glutamic acid | + |
| | Benzoic acid | + |
| | m-hydroxybenzoic acid | + |
| | Sodium salicinate | – |
| | 2,3-Butylene glycol | – |

When these results were taxonomically examined in the same manner based on *Bergey's Manual of Systematic Bacteriology*, it was found that this strain belongs to the genus Pseudomonas but the properties thereof did not coincide with those of standard strains. Therefore, this strain was named Pseudomonas sp. SD811.

Pseudomonas sp. SD812

Morphology

| | | |
|---|---|---|
| (1) | Shape and size of cell | rod 0.5–0.8 μm × 1.5–3.0 μm |
| (2) | Motility | motile |
| (3) | Gram staining | negative |
| (4) | Spore | none |
| (5) | Bacteriolysis by 3% KOH | positive |
| Physiological activity: | | |
| (1) | Aminopeptidase | positive |
| (2) | Oxidase | positive |
| (3) | Catalase | positive |
| (4) | Production of indole | negative |
| (5) | VP Test | negative |
| (6) | Reduction of nitrate | negative |
| (7) | Denitrification | negative |
| (8) | Use of citric acid (Simons) | positive |
| (9) | Urease | positive |
| (10) | Phenylalanine deaminase | negative |
| (11) | Use of malonic acid | positive |
| (12) | Production of levan from sucrose | negative |
| (13) | Lecithinase | negative |
| (14) | Hydrolysis of starch | negative |
| (15) | Hydrolysis of gelatin | negative |
| (16) | Hydrolysis of casein | negative |
| (17) | Hydrolysis of DNA | negative |
| (18) | Hydrolysis of Tween 80 | negative |
| (19) | Hydrolysis of exrin | negative |
| (20) | Growth | |
| | Behavior to oxygen | obligately aerobic |
| | Growth at 37° C. | – |
| | Growth at 41° C. | – |
| | Growth at pH 5.6 | + |
| | Growth in Mac-Conkey-Agar medium | – |
| | Growth in SS-Agar medium | – |
| | Growth in Cetrimid-Agar | – |
| (21) | Production of dye | |
| | Nondiffusive | positive |
| | Diffusive | negative |
| | Fluorescent | negative |
| | Pyrocyanine | negative |
| (22) | OF Test | no decomposition of sugar |
| (23) | Formation of acids | |
| | Glucose | negative |
| | Fructose | negative |
| | Xylose | negative |
| (24) | ONPG (β-galactosidase) | negative |
| (25) | Arginine dihydrolase | negative |
| (26) | Production of gas from glucose | negative |
| (27) | Tyrosine decomposition | positive |
| (28) | Growth factor request | none |
| (29) | Use of various carbon compounds | |
| | Acetic acid | + |
| | Adipic acid | + |
| | Capric acid | – |

-continued

| | | |
|---|---|---|
| | Citric acid | + |
| | Citraconic acid | − |
| | Glycolic acid | + |
| | Levulinic acid | − |
| | Maleic acid | + |
| | Malonic acid | + |
| | Mesaconic acid | + |
| | Muconic acid | + |
| | Phenylacetic acid | + |
| | Saccharic acid | + |
| | Sebacic acid | + |
| | D-Tartaric acid | − |
| | m-Tartaric acid | + |
| | L-Arabinose | − |
| | Cellobiose | − |
| | Fructose | − |
| | D-Fucose | − |
| | Glucose | − |
| | Mannose | − |
| | Maltose | − |
| | Ribose | − |
| | Rhamnose | − |
| | Xylose | − |
| | Mannitol | − |
| | Gluconic acid | + |
| | 2-Ketogluconic acid | + |
| | N-Acetylglucosamine | − |
| | Tryptamine | − |
| | Ethanolamine | − |
| | D-Alanine | + |
| | L-Ornithine | − |
| | L-Serine | − |
| | L-Threonine | + |
| | Glutamic acid | + |
| | Benzoic acid | + |
| | m-hydroxybenzoic acid | + |
| | Sodium salicinate | − |
| | 2,3-Butylene glycol | − |

When these results were taxonomically examined in the same manner based on *Bergey's Manual of Systematic Bacteriology*, it was found that this strain belongs to the genus Pseudomonas but the properties thereof did not coincide with those of standard strains. Therefore, this strain was named Pseudomonas sp. SD812.

Burkholderia sp. SD816
Morphology

| | | |
|---|---|---|
| (1) | Shape and size of cell | rod |
| (2) | Motility | motile |
| (3) | Gram staining | negative |
| (4) | Spore | none |
| (5) | Flagella | Flagallation state is unknown. |

Physiological activity:

| | | |
|---|---|---|
| (1) | Oxidase | positive |
| (2) | Catalase | positive |
| (3) | Cleavage of protocatechinic acid | ortho type |
| (4) | Reduction of nitrate | negative |
| (5) | Denitrification | negative |
| (6) | Accumulation of PHB | positive |
| (7) | Hydrolysis of starch | negative |
| (8) | Hydrolysis of gelatin | negative |
| (9) | Growth | |
| | Behavior to oxygen | obligately aerobic |
| | Growth at 40° C. | + |
| (10) | Production of dye | |
| | Hue of colony | no production of characteristic colonial dye |
| | Production of water-soluble dye | negative |

-continued

| | | |
|---|---|---|
| (11) | OF Test | no decomposition of sugar |
| (12) | Arginine dihydrolase | negative |
| (13) | Use of various carbon compounds | |
| | Levulinic acid | − |
| | Mesaconic acid | − |
| | D-Tartaric acid | + |
| | Ribose | + |
| | Rhamnose | + |
| | Xylose | + |
| | Tryptamine | − |
| | 2,3-Butylene glycol | − |
| (14) | Quinone type | Q-8 |
| (15) | GC content of DNA in cell (mol %) | 62 |

When these results were taxonomically examined in the same manner based on *Bergey's Manual of Systematic Bacteriology* (1986, 1994), it was found that this strain belongs to the genus Burkholderia but the properties thereof did not coincide with those of standard strains. Therefore, this strain was named Burkholderia sp. SD816.

α-Halocarbonyl compounds having an α,β-carbon-carbon double bond, which can be suitably used in the present invention, is represented by the following formula (1):

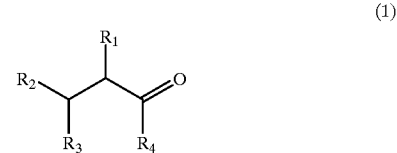

(1)

wherein $R_1$ represents a halogen atom, preferably a chlorine atom or a bromine atom; $R_2$ and $R_3$ each independently represents a hydrogen atom, a halogen atom, a linear or branched aliphatic hydrocarbon group having from 1 to 6 carbon atoms, a linear or branched alkoxy group having from 1 to 6 carbon atoms, a hydroxyl group, a carboxyl group, an aromatic group which may be substituted, or a saturated or unsaturated nitrogen-, oxygen- or sulfur-containing heterocyclic group, preferably a hydrogen atom; $R_4$ represents a hydroxyl group, a linear or branched alkoxy group having from 1 to 4 carbon atoms, or a primary, secondary or tertiary amino group, preferably a hydroxyl group.

Specific examples of the compounds include α-chloroacrylic acid, α-bromoacrylic acid, 2-chloro-2-butenoic acid, 2-bromo-2-butenoic acid, 2-chloro-2-pentenoic acid, 2-bromo-2-pentenoic acid, and the methyl ester and the ethyl ester thereof. Among these, α-chloroacrylic acid and α-bromoacrylic acid are preferred.

In the present invention, the reaction is performed by contacting a microorganism belonging to the genus Pseudomonas or Burkholderia, specifically a microorganism such as Pseudomonas sp. SD811 or Burkholderia sp. SD816 strain, with an α-halocarbonyl compound having an α,β-carbon-carbon double bond to reduce the carbon-carbon double bond, thereby producing a corresponding α-halo-α,β-saturated carbonyl compound.

For the reduction of the carbon-carbon double bond of an α-halocarbonyl compound having an α,β-carbon-carbon double bond performed in the present invention, a microbial cell obtained by the cultivation according to the above-described method or a microbial product of the microorganism, such as a cell-free extract obtained by disrupting a cell culture according to the above-described method, may be used under conditions such that the reducing activity of the microorganism can be stably achieved.

More specifically, in the case of using a cell obtained by cultivation, an α-halocarbonyl compound having an α, β-carbon-carbon double bond is continuously or batchwise added to a culture suspension as a substrate to a concentration of from 0.1 to 10%, preferably from 0.2 to 2%, and cultivation is performed at a growth temperature of from 15 to 35° C., preferably from 25 to 30° C., thereby producing a corresponding α,β-saturated carbonyl compound in the culture suspension.

Alternatively, the culture obtained by the above-described method is subjected to centrifugation or the like to recover cells and the cells are suspended in an appropriate solution, for example, an aqueous solution such as a diluted pH buffer solution. To this suspension, an α-halocarbonyl compound having an α,β-carbon-carbon double bond is continuously or batchwise added as a substrate to a concentration, for example, of from 0.1 to 10% and reacted at a temperature of from 15 to 50° C., preferably from 25 to 30° C., while adjusting the reaction pH to from 6.0 to 9.0, preferably from 6.5 to 7.3, thereby producing a corresponding α-halo-α,β-saturated carbonyl compound in the cell suspension.

In the case of using a microbial product of a microorganism, for example, the culture obtained by the above-described culture method is subjected to centrifugation to recover cells, the cells are disrupted by French pressing or a like method to obtain a cell-free extract, and the cell-free extract is added to a reaction mixture containing an α-halocarbonyl compound having an α, β-carbon-carbon double bond as a substrate, in a concentration of from 0.1 to 10%, preferably from 0.2 to 2%, and also containing an ingredient effective in maintaining the pH of the reaction mixture, in a concentration of from 10 mM to 1 M, and reacted with continuous or batch addition of substrate at a temperature of from 15 to 50° C., preferably from 28 to 35° C., thereby producing a corresponding α, β-saturated carbonyl compound.

In the present invention, the reaction may be performed while continuously or batchwise adding a substance effective in maintaining the activity of reducing the α-halocarbonyl compound having an α,β-carbon-carbon double bond, for example, a compound capable of being oxidized by the microorganism used, such as sugar or organic acid, preferably glucose or L-lactic acid, by itself or as a mixed solution with an α-halocarbonyl compound having an α, β-carbon-carbon double bond to have a concentration of from 0.1 to 10%, preferably from 0.2 to 1% during the reaction. The ratio of the α-halocarbonyl compound having an α, β-carbon-carbon double bond to the additional substance to be oxidized may be freely selected between 1:1 and 20:1 on a molar basis. By this addition of sugar or organic acid, the reaction time may be prolonged and in turn, the concentration of the objective product α-halo-α,β-saturated carbonyl compound in the reaction suspension may be increased. This is advantageous for collecting the product by isolation. Except for the cultivation time, the reaction may be performed either in an aerobic or anaerobic environment. The ratio of the cell or cell-free extract to the α-halocarbonyl compound having an α,β-carbon-carbon double bond as the substrate, and the timing and rate or frequency of addition may be freely selected in the range capable of attaining the completion of reaction within the objective time.

In the present invention, the α-halo-α,β-saturated carbonyl compound obtained by the reduction of an α-halocarbonyl compound having an α,β-carbon-carbon double bond is a metabolic intermediate for the microorganism used and may be further decomposed. For example, some microorganisms relatively swiftly decompose the α-chloropropionic acid produced from α-chloroacrylic acid. If the case is so, the decomposition reaction may be stopped by using a mutant defective in decomposing activity, decreasing the pH value, heat-treating the cells or cell-free extract, or adding an appropriate inhibitor of the decomposing enzyme. To speak more specifically, under the conditions where an α-chloropropionic acid is produced from an α-chloroacrylic acid at an optimal rate, the Pseudomonas sp. SD811 strain usually swiftly decomposes the α-chloropropionic acid produced in the culture suspension or reaction suspension, whereby the conversion ratio into α-chloropropionic acid based on the α-chloroacrylic acid decreases. However, since the optimal reaction pH at the stage of producing α-chloropropionic acid from α-chloroacrylic acid is from 5 to 7 and the optimal reaction pH at the decomposition stage of α-chloropropionic acid is from 7.0 to 7.3, thus, the optimal reaction pH at the decomposition stage of α-chloropropionic acid is higher than the optimal reaction pH at the stage of producing α-chloropropionic acid from α-chloroacrylic acid. Accordingly, the amount of α-chloropropionic acid produced can be increased by performing the reaction at a low pH of from 5 to 7 which is the optimal reaction pH range for the stage of producing α-chloropropionic acid. Furthermore, certain enzymes which decompose the α-chloropropionic acid are known to be effectively inhibited by hydroxylamine (see, Soda K. et al., *J. Biol. Chem.*, 272, 3363–3368 (1997)) and also in the present invention, the decomposition reaction can be inhibited by adding an appropriate amount of hydroxylamine to the culture suspension or reaction suspension.

The cell or cell-free extract of the microorganism for use in the present invention may be used by fixing it to an immobilizing support of various types by a commonly known method such as adsorption, inclusion or crosslinking. The kind of the support is not particularly limited and for example, a polysaccharide-type material such as cellulose, a polymer-type material, or a protein-type material such as collagen, may be used.

The α-halocarbonyl compound having an α,β-carbon-carbon double bond for use in the present invention is a molecule prochiral at the α-position, however, by reducing the carbon-carbon double bond, a corresponding α-halo-α,β-saturated carbonyl compound having an absolute S form configuration at the α-position may be produced.

The culture method of the microorganism used in the present invention is not particularly limited as long as aerobic microorganisms in general can grow. The carbon source of the medium may be any source as long as the above-described microorganisms can be used and examples thereof include saccharides, acetic acid, lactic acid and a mixture thereof. Examples of nitrogen sources which can be used include ammonium salts such as ammonium sulfate and ammonium phosphate, nitrogen-containing compounds such as meat extract and yeast extract, and mixtures thereof.

In addition to these ingredients, nutrients commonly used in cultivation, such as inorganic salts, trace metal salts and vitamins, may be used in the medium by appropriately mixing them. Furthermore, if desired, a factor of accelerating the growth of the microorganism and an ingredient effective in maintaining the pH of the medium may be added. Also, a compound effective in increasing the reductive activity of the microorganism, for example, an α-halocarbonyl compound having an α,β-carbon-carbon double bond, such as α-chloroacrylic acid, may be used as a sole carbon source or may be used by mixing it with a plurality of carbon sources.

The microorganism for use in the present invention may be cultured under aerobic conditions used for the cultivation of almost all aerobes or facultative anaerobes, for example, under conditions such that the pH of the medium is from 5.5 to 8.0, preferably from 6.5 to 7.0, and the growth temperature is from 15 to 35° C., preferably from 25 to 30° C. The cultivation time is, for example, from 1 to 144 hours, preferably from 12 to 72 hours.

The α-halo-α,β-saturated carbonyl compound produced according to the present invention may be obtained using an ordinary purification method such as organic solvent extraction or distillation. For example, α-chloropropionic acid produced from α-chloroacrylic acid may be obtained by subjecting the culture suspension or reaction suspension to organic solvent extraction, distillation or the like. Furthermore, although the α-halocarbonyl compound having an α,β-carbon-carbon double bond is a molecule prochiral at the α-position, the α-halo-α,β-saturated carbonyl compound produced by the reducing method of the present invention is a chiral compound and it is advantageous to determine the purity of the enantiomer thereof by GC and/or HPLC with a chiral column or by a polarimeter.

As described in the foregoing, in the method of the present invention for producing a corresponding α-halo-α, β-saturated carbonyl compound having an absolute S form configuration from an α-halocarbonyl compound having an α, β-carbon-carbon double bond by reducing the carbon-carbon double bond, an aerobe or facultative anaerobe is used, therefore, the method is favored with high profitability, good operability and excellent processing safety.

The present invention is described in greater detail below by referring to the Examples, however, the present invention should not be construed as being limited to these Examples.

EXAMPLE 1
Detection of Activity of Reducing α-Halocarbonyl Compound Having an α,β-Carbon-Carbon Double Bond Microorganisms cultured by accumulative cultivation or accumulative acclimatization and isolated were cultured at 30° C. using a medium obtained by adding 0.2% of α-chloroacrylic aid or α-chloro-α,β-butenoic acid as a carbon source to a basal medium containing yeast extract (0.5 g/l), ammonium sulfate (2 g/l), sodium dihydrogenphosphate (1 g/l), dipotassium hyrogenphosphate (1 g/l) and magnesium sulfate (0.1 g/l) (for the isolation of some microorganisms which grow only in a high salt concentration medium, a medium obtained by adding sodium chloride in a concentration of from 10 to 20% to the above-described basal medium was used as the basal medium). Whether or not α-chloropropionic acid or α-chlorobutyric acid as the corresponding reduction product appeared in the culture suspension was examined using gas chromatography. From each solution, 0.5 ml was sampled at a specific time and centrifuged to remove cells. Thereafter, 0.4 ml of the supernatant was mixed with 0.4 ml of 2N HCl and analyzed under the following conditions:

Apparatus: GC-7A (manufactured by Shimadzu Seisakusho)
Column: Thermon-3000/SHINCARBON A, 2.6 mm×2.1 m
Carrier gas: nitrogen, 50 ml/min.
Detection: FID
Column temperature: 200° C. (constant)
Injection: 2 to 10 μl, 260° C.
Recording: CHROMATOCODER 12 (SIC)

By this detection, peaks appeared swiftly after the initiation of cultivation at the position of α-chloropropionic acid or α-chlorobutyric acid accompanying the consumption of α-chloroacrylic in the culture suspension of a plurality of microorganisms. The peaks were analyzed by GC-MS and found to coincide with the mass spectrum of α-chloropropionic acid or α-chlorobutyric acid as the standard substance, therefore, the products were confirmed to be α-chloropropionic acid or α-chlorobutyric acid. The genera of microorganisms of which cultivation brought about generation of the reduction product were identified, as a result, it was found that microorganisms belonging to various genera have reducing activity. Microorganisms recognized to have the activity were aerobes or facultative anaerobes belonging to the genera Acetobacter, Actinomyces, Acinetobacter, Agrobacterium, Aeromonas, Alcaligenes, Arthrobacter, Azotobacter, Bacillus, Brevibacterium, Burkholderia, Cellulomonas, Corynebacterium, Enterobacter, Enterococcus, Escherichia, Flavobacterium, Gluconobacter, Halobacteium, Halococccus, Klebsiella, Lactobacillus, Microbacterium, Micrococcus, Micropolyspora, Mycobacterium, Nocardia, Pseudomonas, Pseudonocardia, Rhodococcus, Rhodobacter, Serratia, Staphylococcus, Streptococcus, Streptomyces and Xanthomonas. Strains of the genus Pseudomonas prevailed in the strains recognized. Microorganisms relatively surpassed in the amount of the reduction product were the microorganisms belonging to the genera Pseudomonas and Burkholderia. With any strain, the reduction product recognized in the culture suspension was in a small amount (0.01% or less), therefore, the following elite strains were examined for optimization of product accumulating conditions.

EXAMPLE 2
(1) Cultivation of Pseudomonas sp. SD811 Strain

Pseudomonas sp. SD811 strain was cultured in a medium containing the following ingredients (amount: g/L): α-chloroacrylic acid (2), yeast extract (0.5), ammonium sulfate (2), sodium dihydrogenphosphate (1), dipotassium hydrogenphosphate (1) and magnesium sulfate (0.1). The medium was prepared as follows. All ingredients except for α-chloroacrylic acid and magnesium sulfate were dissolved in 950 ml of water and after the pH was adjusted to 7.0, the solution was poured into a 5 l-volume flask and sterilized at 121° C. for 20 minutes. After the temperature of this medium decreased to about 70° C., a solution obtained by dissolving α-chloroacrylic acid and magnesium sulfate in 50 ml of water, adjusted to a pH of 7.0 and then sterilized through a sterilization filter was mixed with the medium prepared above. Without supplying oxygen or adjusting the pH any more, a 5% seed culture (OD 660 nm: 1.10) was inoculated in this medium and the strain was cultured at 30° C.

(2) Detection of α-Chloropropionic Acid in α-Chloroacrylic Acid Culture Medium

During cultivation of the Pseudomonas sp. SD811 strain with α-chloroacrylic acid, 0.5 ml was sampled at a specific time. The sample was centrifuged to remove cells and 0.4 ml of the supernatant was mixed with 0.4 ml of 2N HCl. The solution obtained was analyzed under the conditions described in Example 1.

By the detection, a peak appeared swiftly after the initiation of culturing at the position of α-chloropropionic acid accompanying the consumption of α-chloroacrylic acid in the culture suspension of Pseudomonas sp. SD811 strain. The production was about 0.02% of the culture suspension at the maximum time and the conversion ratio based on the substrate α-chloroacrylic acid was about 10%.

EXAMPLE 3

(1) Cell Suspension Reaction 1 Using α-Chloroacrylic Acid as Substrate

A culture obtained by culturing the Pseudomonas sp. SD811 strain in a 1/10 scale of the method in Example 2 was subjected to centrifugation to recover the cells. The cells were suspended in 20 ml of a solution (adjusted to a pH of 7.3) containing 0.2% of α-chloroacrylic acid and 100 mM of phosphate buffer (pH: 7.3) and reacted by shaking at 28° C.

From the reaction mixture, 0.5 ml was sampled at a specific time and centrifuged to remove cells. Thereafter, 0.4 ml of the supernatant and 0.1 ml of 6N HCl were mixed and then the product was extracted with 0.4 ml of ethyl acetate. The sample extracted was analyzed by the method of Example 1. As a result, a peak appeared at the position of α-chloropropionic acid accompanying the consumption of α-chloroacrylic acid in the reaction mixture. The production was about 0.05% of the reaction suspension at the maximum time and the conversion ratio was about 25% based on the substrate α-chloroacrylic acid.

(2) Isolation of α-Chlorogpropionic Acid from Cell Suspension Reaction Using α-Chloroacrylic Acid as Substrate A culture obtained by culturing the Pseudomonas sp. SD811 strain in a 1/5 scale of the method in Example 1 was subjected to centrifugation to recover the cells and the cells were suspended in 100 ml of a solution (adjusted to a pH of 7.3) containing 0.2% of α-chloroacrylic acid and 100 mM of potassium phosphate-sodium hydroxide buffer and reacted by stirring at 28° C. At the time when the α-chloroacrylic acid was exhausted during the reaction, α-chloroacrylic acid was added in a concentration of 0.2% of the reaction mixture and the reaction was continued. From the reaction suspension, 0.5 ml was sampled at a specific time, the product was separated by extraction according to the method of Example 3, and the production of α-chloropropionic acid was monitored by the method of Example 1. After about 9 hours when α-chloroacrylic acid was not detected in the reaction suspension, the reaction was completed and the entire amount of the reaction suspension was subjected to centrifugation to remove cells. To 95 ml of the supernatant obtained, 20 ml of 6N HCl was added, and the product was extracted with 95 ml of ethyl acetate. The ethyl acetate layer was washed with 100 ml of saturated saline and then concentrated by removing ethyl acetate by evaporation. The concentrated sample was analyzed by the method of Example 1, as a result, a slight amount of α-chloroacrylic acid and α-chloropropionic acid were detected. The α-chloropropionic acid present in the concentrated sample was about 100 mg in total and the conversion ratio was about 25% based on the substrate α-chloroacrylic acid.

EXAMPLE 4

(1) Methylation of α-Chloropropionic Acid

When optical resolution is performed by an optical resolution GC column, unmodified carboxylic acid exhibits poor separability due to the effect of the carboxyl group in many cases. Therefore, the product was methyl esterified by a boron trifluoride-methanol complex salt method. More specifically, 4 ml of methanol was added to 3 mg of α-chloropropionic acid and mixed. Thereafter, 1 ml of a 14% methanol solution of boron trifluoride-methanol complex was further added and the resulting solution was refluxed on an oil bath at 80° C. for 1 hour while stirring. After 1 hour, 30 ml of water was added to the reaction mixture and the reactant was extracted with 10 ml of ethyl acetate. The ethyl acetate was then distilled off by a centrifugal evaporator to concentrate the sample to the entire amount of about 0.1 ml. The concentrated sample was analyzed by the method of Example 1 except that the column temperature only was changed to 120° C. As a result, one main peak was observed at the position of methyl α-chloropropionate. By the GC-MS analysis of the peak, the product was identified to be methyl α-chloropropionate.

(2) Optical Resolution GC Analysis of α-Chloropropionic Acid

After the methylation by the above-described method, the S-form α-chloropropionic acid and the R-form α-chloropropionic acid could be successfully separated under the following analysis conditions.

Apparatus: GC-14A (manufactured by Shimadzu Seisakusho)

Column: CP-Chirasil-DEX CB, 0.32 mm I.D.×25 m, df=0.25 mm (manufactured by GL Science K.K.)

Carrier gas: He, 0.38 kg/cm$^2$

Detection: FID, 275° C.

Column temperature: 70° C. (constant)

Injection: 0.1 to 0.2 μl, split, about 1:100, 250° C.

Recording: CHROMATOPACK C-6A (manufactured by Shimadzu Seisakusho)

The methyl α-chloropropionate obtained from the reaction mixture of Example 3 under the above-described conditions was analyzed, then a peak was observed only at the position of S-form methyl α-chloropropionate. The optical purity thereof was 99% or more.

EXAMPLE 5

Cell Suspension Reaction 2 Using α-Chloroacrylic Acid as Substrate

A culture obtained by culturing Pseudomonas sp. SD811 strain in a 1/10 scale of the method as described in Example 2 was subjected to centrifugation to recover the cells. The cells were suspended in 20 ml of a solution (adjusted to a pH of 5.7) containing 0.2% of α-chloroacrylic acid and 100 mM of phosphate buffer (pH: 5.7) and reacted by shaking at 28° C. From the reaction mixture, 0.5 ml was sampled at a specific time and centrifuged to remove cells. Thereafter, 0.4 ml of the supernatant and 0.1 ml of 6N HCl were mixed and then the product was extracted with 0.4 ml of ethyl acetate. The sample extracted was analyzed by the method of Example 1, as a result, a peak appeared at the position of α-chloropropionic acid accompanying the consumption of α-chloroacrylic acid in the reaction mixture. The production was about 0.08% of the reaction suspension at the maximum time and the conversion ratio was about 41% based on the substrate α-chloroacrylic acid.

EXAMPLE 6

Preparation of α-Chloropropionic Acid-Undecomposable Mutant

A culture obtained by culturing Pseudomonas sp. SD811 strain in a 1/200 scale of the method in Example 2 was subjected to centrifugation to recover the cells and the cells were washed with physiological saline. The washed cells were re-suspended in 1 ml of 10 to 100 mM phosphate buffer (pH: 7). To the resulting cell suspension, N-methyl-N'-nitro-N-nitrosoguanidine (NTG) was added to a final concentration of from 50 to 100 ppm and the cells were treated at room temperature for from 2 to 20 minutes. After the treatment, the cell suspension was subjected to centrifugation to recover the cells, the cells were washed with sterilized physiological saline, and the entire amount thereof was inoculated in 5 ml of an L medium (polypeptone: 10 g/l, yeast extract: 5 g/l, sodium chloride: 5 g/l, pH: 7) and cultured by shaking at 28° C. After the completion of cultivation, the culture was subjected to centrifugation to recover the cells and the cells were suspended in a 20% glycerin solution. The suspension was equally divided by an appropriate amount and frozen to prepare glycerin stocks for selection of a mutant.

EXAMPLE 7
Selection of α-Chloropropionic Acid-Undecomposanble Mutant

A glycerin stock for selection of a mutant prepared above was inoculated in 5 ml of a medium used in the method of Example 2 and cultured at 28° C. for 5 hours. At the time when the turbidity was increased as high as several times, penicillin G was added to the culture suspension in an amount of giving a final concentration of from 100 to 1,000 ppm and the cultivation was continued at 28° C. After the cultivation for from 5 to 16 hours, the culture suspension was subjected to centrifugation to recover the cells. The cells were washed twice with sterilized physiological saline and the entire amount thereof was inoculated in 5 ml of L-broth and cultured by shaking at 28° C. an entire day and night.

The culture suspension obtained above was diluted, spread on a medium the same as used in Example 2 except that the α-chloroacrylic acid as a carbon source was replaced by an equivalent amount of lactic acid and the medium was solidified by adding 2% agar, and cultured at 28° C. After 1 or 2 days, colonies formed on the plate were replicated on the medium used as described in Example 2 which was solidified by adding 2% agar, and cultured at 28° C. for 1 or 2 days. Strains which grew on the lactic acid plate but did not grow on the α-chloroacrylic acid plate were isolated as candidates for the α-chloropropionic acid-undecomposable mutant.

The candidate strains each isolated were inoculated by an inoculating loop in 5 ml of a medium the same as used in Example 2 except that 2 g/l of lactic acid was added as a carbon source capable of growing, and cultured by shaking at 28° C. The culture suspensions obtained were analyzed by the method of Example 1, as a result, the production maximum of α-chloropropionic acid produced in the culture was distributed depending on the candidate strains, however, the production maximum with the mutant of Pseudomonas sp. SD811 was about 0.17% of the culture suspension and the conversion ratio was about 85% based on the substrate α-chloroacrylic acid. With the variation strain of Burkholderia sp. SD816, the production maximum was about 0.15% of the culture suspension and the conversion ratio was about 75% based on the substrate α-chloroacrylic acid. These strains were selected as the α-chloropropionic acid-undecomposable mutant.

EXAMPLE 8
Cell Suspension Reaction 3 Using α-Chloroacrylic Acid as Substrate The α-chloropropionic acid-undecomposable mutant of Pseudomonas sp. SD811 and the α-chloropropionic acid-undecomposable mutant of Burkholderia sp. SD816 each was cultured in the same medium of lactic acid as used in Example 7, and each of the cultures obtained was subjected to centrifugation to recover the cells. The cells of each strain were suspended in 20 ml of a solution (adjusted to a pH of 7.3) containing 0.2% of α-chloroacrylic acid and 100 mM of phosphate buffer (pH: 7.3) and reacted by shaking at 28° C.

From each reaction suspension, 0.5 ml was sampled at a specific time and centrifuged to remove cells. To 0.4 ml of the supernatant, 0.1 ml of 6N HCl was mixed and then, the product was extracted with 0.4 ml of ethyl acetate. The sample extracted was analyzed by the method of Example 1. As a result, a peak appeared at the position of α-chloropropionic acid accompanying the consumption of α-chloroacrylic acid in the reaction suspension. With the mutant of Pseudomonas sp. SD811, the production was about 0.19% of the reaction suspension at the time when the α-chloroacrylic acid disappeared in the reaction mixture and the conversion ratio was about 95% based on the substrate α-chloroacrylic acid. With the mutant of Burkholderia sp. SD816, those were about 0.2% and about 100%, respectively. In either case, the α-chloropropionic acid produced did not decrease with the passing of time. The optical activity of the α-chloropropionic acid was analyzed according to the method of Example 4. As a result, in both cases, the product was an S-form compound and the optical purity thereof was 99% or more.

EXAMPLE 9
Cell Suspension Reaction 4 Using α-Chloroacrylic Acid as Substrate The α-chloropropionic acid-undecomposable mutant of Pseudomonas sp. SD811 and the α-chloropropionic acid-undecomposable mutant of Burkholderia sp. SD816 each was cultured in 100 ml of a medium obtained by adding 0.2% of glucose as a carbon source to the basal medium used in Example 2, and the cultures obtained each was subjected to centrifugation to recover the cells. The cells of each strain were suspended in 20 ml of a solution (adjusted to a pH of 7.3) containing 0.2% of α-chloroacrylic acid and 100 mM of phosphate buffer (pH: 7.3) and reacted by shaking at 28° C.

From each reaction suspension, 0.5 ml was sampled at a specific time and centrifuged to remove cells. To 0.4 ml of the supernatant, 0.1 ml of 6N HCl was mixed and then, the product was extracted with 0.4 ml of ethyl acetate. The sample extracted was analyzed by the method of Example 1. As a result, after the lag time of a few hours at the initial stage when the reaction was started, a peak appeared at the position of α-chloropropionic acid accompanying the consumption of α-chloroacrylic acid in the reaction suspension. With the mutant of Pseudomonas sp. SD811, the production was about 0.19% of the reaction suspension at the time when the α-chloroacrylic acid disappeared in the reaction mixture and the conversion ratio was about 95% based on the substrate α-chloroacrylic acid. With the mutant of Burkholderia sp. SD816, those were about 0.2% and about 100%, respectively.

EXAMPLE 10
Cultivation in Jar Fermenter

The α-chloropropionic acid-undecomposable mutant of Burkholderia sp. SD816 was cultured for 16 hours in 100 ml of a medium (5×medium, pH: 7.0) the same as used in Example 9 except that the medium ingredients each had a five-fold concentration. The culture obtained was inoculated in 2 L of 5×medium filled in a 5 L-volume jar fermenter and cultured at 28° C., 800 rpm and an aeration rate of 1 ml/min. When from about 15 to 20 hours passed after the initiation of cultivation, the glucose initially charged were completely consumed, accordingly, a 5 to 20% glucose solution, a 5 to 15% ammonium sulfate solution and a 1 to 5% yeast extract solution as individual solutions or a mixed solution were further continuously added by means of PERISTACK pump. The addition rate was controlled so that the glucose concentration of from 0.02 to 2% could be maintained during the addition. The pH of the culture suspension was adjusted by a 20% aqueous ammonia to lie in the range of from 6.3

EXAMPLE 11
Cell Suspension Reaction 5 Using α-Chloroacrylic Acid as Substrate The α-chloropropionic acid-undecomposable mutant of Burkholderia sp. SD816 was cultured according to the method of Example 10. When from 48 to 72 hours passed after the initiation of cultivation, the addition of glucose and the like was stopped to interrupt growth. To this culture suspension, α-chloroacrylic acid was added to a final concentration of about 0.2% and reacted under the same conditions as in the cultivation. From the reaction suspension, 0.5 ml was sampled at a specific time and centrifuged to remove cells. Thereafter, 0.4 ml of the supernatant and 0.4 ml of 2N HCl were mixed and the α-chloroacrylic acid concentration in the solution was determined under the following conditions.

- Apparatus: LC-9A (manufactured by Shimadzu Seisakusho)
- Column: ODSpak F-511/4.6 mm×250 mm (Shodex)
- Eluent acetonitrile/water=⅖+0.1% trifluoroacetic acid, 1 ml/min.
- Detection: SPD-6AV UV-VIS Spectrophotometer (manufactured by Shimadzu Seisakusho)
- Column temperature: 25° C.
- Injection: Autosampler Model 23 (SIC) with 20 μl sample loop
- Recording: CHROMATOCODER 12 (SIC)

In this reaction, after the lag time of from 3 to 7 hours at the initial stage when the reaction was started, consumption of α-chloroacrylic acid started. When the α-chloroacrylic acid concentration became about 0.02%, α-chloroacrylic acid was further added so that the α-chloroacrylic acid concentration could be increased to about 0.2%. This operation was repeated until the consumption of α-chloroacrylic acid substantially terminated. The accumulative production of α-chloropropionic acid after 32 hours where the reaction was substantially stopped was from about 1.0 to 1.2% of the reaction suspension and the conversion ratio was about 97% based on the substrate α-chloroacrylic acid. The optical activity of the α-chloropropionic acid accumulated was analyzed according to the method of Example 4. As a result, the product was an S-form compound and the optical purity thereof was 99% or more.

EXAMPLE 12
Cell Suspension Reaction 6 Using α-Chloroacrylic Acid as Substrate The α-chloropropionic acid-undecomposable mutant of Burkholderia sp. SD816 was cultured for from 48 to 72 hours according to the method of Example 10 and the culture obtained was subjected to centrifugation to recover the cells. The cells were suspended in 2 l of a solution (adjusted to a pH of 7.1) containing 0.2% α-chloroacrylic acid and 60 mM of phosphate buffer (pH: 7.1) and reacted at 28° C., 800 rpm and an aeration rate of 1 ml/min. From the reaction suspension, 0.5 ml was sampled at a specific time and centrifuged to remove cells. Thereafter, 0.4 ml of the supernatant and 0.4 ml of 2N HCl were mixed and the α-chloroacrylic acid concentration in the solution was determined by the method described in Example 11.

In this reaction, after a lag time of from 3 to 7 hours at the initial stage when the reaction was started, consumption of α-chloroacrylic acid started. When the α-chloroacrylic acid concentration became about 0.02%, α-chloroacrylic acid was further added so that the α-chloroacrylic acid concentration could be increased to about 0.2%. This operation was repeated until the consumption of α-chloroacrylic acid substantially terminated. The accumulative production of α-chloropropionic acid after 28 hours where the reaction was substantially stopped was from about 0.8 to 1.0% of the reaction suspension and the conversion ratio was about 98% based on the substrate α-chloroacrylic acid.

EXAMPLE 13
Cell Suspension Reaction 7 Using α-Chloroacrylic Acid as Substrate The α-chloropropionic acid-undecomposable mutant of Burkholderia sp. SD816 was cultured for from 48 to 72 hours according to the method of Example 10 and the culture obtained was subjected to centrifugation to recover the cells. The cells were suspended in 2 l of 60 mM phosphate buffer (pH: 7.1) and reacted at 28° C., 800 rpm and an aeration rate of 1 ml/min while adding from 5 to 10% of an α-chloroacrylic acid solution to the cell suspension little by little by means of PERISTACK pump. From the reaction suspension, 0.5 ml was sampled at a specific time and centrifuged to remove cells. Thereafter, 0.4 ml of the supernatant and 0.4 ml of 2N HCl were mixed and the α-chloroacrylic acid concentration in the solution was determined by the method described in Example 11.

In this reaction, after a lag time of from 5 to 10 hours at the initial stage when the reaction was started, consumption of α-chloroacrylic acid started. The addition rate of the α-chloroacrylic acid solution was controlled in accordance with the consuming rate so that the α-chloroacrylic acid concentration could be in the range of from about 0.02 to 0.2%, preferably around 0.1%. This operation was continued until the consumption of α-chloroacrylic acid substantially terminated. The accumulative production of α-chloropropionic acid after 24 hours where the reaction was substantially stopped was from about 0.8 to 1.2% of the reaction suspension and the conversion ratio was about 95% based on the substrate α-chloroacrylic acid.

EXAMPLE 14
Cell Suspension Reaction 8 Using α-Chloroacrylic Acid as Substrate The α-chloropropionic acid-undecomposable mutant of Burkholderia sp. SD816 was cultured for from 48 to 72 hours according to the method of Example 10 and the culture obtained was subjected to centrifugation to recover the cells. The cells were suspended in 2 l of 60 mM phosphate buffer (pH: 7.1) and reacted at 28° C., 800 rpm and an aeration rate of 1 ml/min while adding from 5 to 10% of an α-chloroacrylic acid solution to the cell suspension little by little by means of PERISTACK pump. At the same time, from 5 to 10% of a sodium lactate solution was added alone or as a mixed solution with α-chloroacrylic acid little by little by means of PERISTACK pump. From the reaction suspension, 0.5 ml was sampled at a specific time and centrifuged to remove cells. Thereafter, 0.4 ml of the supernatant and 0.4 ml of 2N HCl were mixed and the α-chloroacrylic acid concentration in the solution was determined by the method described in Example 11. The concentration of lactic acid was determined using lactate dehydrogenase. The pH of the reaction system was adjusted to from 6.5 to 7.3 using 20% aqueous ammonia and 2N HCl.

In this reaction, after the lag time of from 5 to 10 hours at the initial stage when the reaction was started, consumption of α-chloroacrylic acid started. Lactic acid was swiftly consumed immediately after the initiation of reaction. The addition rate of the α-chloroacrylic acid solution was controlled in accordance with the consuming rate so that the α-chloroacrylic acid concentration could lie in the range of from about 0.02 to 0.2%, preferably around 0.1%. At the same time, the added amount of lactic acid was controlled to prevent the concentration from exceeding 0.4%. This operation was continued for about 60 hours. In this Example, the reduction clearly continued and proceeded at a constant rate even after about 60 hours because lactic acid was present together. The accumulative production of α-chloropropionic acid after the 60-hour reaction was from about 2.8 to 3.2% of the reaction suspension and the conversion ratio was about 99% or more based on the substrate α-chloroacrylic acid.

EXAMPLE 15
Cell Suspension Reaction 9 Using α-Chloroacrylic Acid as

The α-chloropropionic acid-undecomposable mutant of Burkholderia sp. SD816 was cultured for from 48 to 72 hours according to the method of Example 10 and the culture obtained was subjected to centrifugation to recover the cells. The cells were suspended in 2 l of 60 mM phosphate buffer (pH: 7.1) and reacted at 28° C., 800 rpm and an aeration rate of 1 ml/min while adding a mixed aqueous solution containing 10% of an α-chloroacrylic acid and 10% of glucose to the cell suspension little by little by means of PERISTACK pump. From the reaction suspension, 0.5 ml was sampled at a specific time and centrifuged to remove cells. Thereafter, 0.4 ml of the supernatant and 0.4 ml of 2N HCl were mixed and the α-chloroacrylic acid concentration in the solution was determined by the method described in Example 11. In the determination of the glucose concentration, the reaction supernatant as the original solution obtained after the centrifugation was used intact and subjected to the measurement by a glucose analyzer. The pH of the reaction system was adjusted to from 6.5 to 7.3 using 20% aqueous ammonia and 2N HCl. In this reaction, after a lag time of from 6 to 12 hours at the initial stage when the reaction was started, consumption of α-chloroacrylic acid started. The glucose was swiftly consumed particularly right after the initiation of reaction but after the reducing activity was induced, the glucose was consumed at a constant rate. The addition rate of the mixed solution was controlled so that the α-chloroacrylic acid concentration could lie in the range of from about 0.02 to 0.2%, preferably around 1%, and at the same time, the glucose concentration could be prevented from exceeding 0.4%. This operation was continued for about 60 hours. In this Example, the reduction reaction clearly continued and proceeded at a constant rate even after about 60 hours because glucose was present together. The conversion ratio was about 99% or more based on the α-chloroacrylic acid after the 60-hour reaction.

EXAMPLE 16
Cell Suspension Reaction 10 Using α-Chloroacrylic Acid as Substrate

The α-chloropropionic acid-undecomposable mutant of Burkholderia sp. SD816 was cultured for from 48 to 72 hours in the ½ scale of the method of Example 10 and the culture obtained was subjected to centrifugation to recover the cells. The cells were suspended in 1 l of a solution (adjusted to a pH of 7.1) containing 0.2% of α-chloroacrylic acid, 0.2% of glucose and 60 mM of phosphate buffer (pH: 7.1), and reacted at 28° C., 800 rpm and an aeration rate of 1 ml/min. At the end point in a lag time of from 5 to 10 hours after the initiation of reaction, air for the aeration was changed to nitrogen gas and thereafter, the reaction was performed in an anaerobic environment. From the reaction suspension, 0.5 ml was sampled at a specific time and centrifuged to remove cells. Then, 0.4 ml of the supernatant and 0.4 ml of 2N HCl were mixed and the α-chloroacrylic acid concentration in the solution was determined by the method described in Example 11. At the same time, the glucose concentration was determined by a glucose analyzer. The pH of the reaction system was adjusted to from 6.5 to 7.3 using 20% aqueous ammonia and 2N HCl.

In this reaction, after a lag time of from 5 to 10 hours at the initial stage when the reaction was started, consumption of α-chloroacrylic acid started. When the α-chloroacrylic acid concentration became about 0.02%, α-chloroacrylic acid or glucose was further added so that the α-chloroacrylic acid concentration could be increased to 0.2% or the glucose concentration could be around 0.1%. This operation was continued for about 60 hours. In this Example, the reduction reaction clearly continued and proceeded at a constant rate even after about 60 hours because a substance to be oxidized was present together. The consumption of glucose showed a marked decrease immediately after the reaction system was changed from an aerobic environment to an anaerobic environment and the total consumption was reduced to about ¹⁄₁₀ or less that in the reaction in an aerobic environment. The accumulative production of α-chloropropionic acid after the 60-hour reaction was from about 2.5 to 3.2% of the reaction suspension and the conversion ratio was about 99% or more based on the substrate α-chloroacrylic acid.

In the method of the present invention for producing a corresponding α-halo-α,β-saturated carbonyl compound from an α-halocarbonyl compound having an α,β-carbon-carbon double bond by reducing the carbon-carbon double bond, an aerobe or facultative anaerobe is used, therefore, the method is favored with high profitability, good operability and excellent processing safety. Furthermore, according to the method of the present invention, a high-purity α-halo-α, β-saturated carbonyl compound useful as a chiral building block of medical and agricultural chemicals and the like is produced.

While the invention has been described in detail and with reference to specific embodiments thereof, it will be apparent to one skilled in the art that various changes and modifications can be made therein without departing from the spirit and scope thereof.

What is claimed is:

1. A method of producing an α-halo-α,β-saturated carbonyl compound from an α-halocarbonyl compound having an α,β-carbon-carbon double bond by reducing said α,β-carbon-carbon double bond comprising culturing a microorganism belonging to any one of the genera Acetobacter, Actinomyces, Acinetobacter, Agrobacterium, Aeromonas, Alcaligenes, Arthrobacter, Azotobacter, Bacillus, Brevibacterium, Burkholderia, Cellulomonas, Corynebacterium, Enterobacter, Enterococcus, Escherichia, Flavobacterium, Gluconobacter, Halobacterium, Halococcus, Klebsiella, Lactobacillus, Microbacterium, Micrococcus, Micropolyspora, Mycobacterium, Nocardia, Pseudomonas, Pseudonocardia, Rhodococcus, Rhodobacter, Serratia, Staphylococcus, Streptococcus, Streptomyces and Xanthomonas, or a microbial product thereof in the presence of said α-halocarbonyl compound having an α, β-carbon-carbon double bond and recovering said α-halo-α,β-saturated carbonyl compound.

2. The method of producing an α-halo-α,β-saturated carbonyl compound as claimed in claim 1, wherein said method comprises reducing said α,β-carbon on double bond of the α-halocarbonyl compound having an α,β-carbon-carbon double bond using a microorganism belonging to the genus Pseudomonas or a microbial product thereof.

3. The method of producing an α-halo-α,β-saturated carbonyl compound as claimed in claim 1, wherein said method comprises reducing said α,β-carbon-carbon double bond of the α-halocarbonyl compound having an α,β-carbon-carbon double bond using a microorganism belonging to the genus Burkholderia or a microbial product thereof.

4. The method of producing an α-halo-α,β-saturated carbonyl compound as claimed in claim 2, wherein the microorganism belonging to the genus Pseudomonas is Pseudomonas sp. SD810.

5. The method of producing an α-halo-α,β-saturated carbonyl compound as claimed in claim 2, wherein the microorganism belonging to the genus Pseudomonas is Pseudomonas sp. SD811.

6. The method of producing an α-halo-α,β-saturated carbonyl compound as claimed in claim 2, wherein the microorganism belonging to the genus Pseudomonas is Pseudomonas sp. SD812.

7. The method of producing an α-halo-α,β-saturated carbonyl compound as claimed in claim 3, wherein the microorganism belonging to the genus Burkholderia is Burkholderia sp. SD816.

8. The method of producing an α-halo-α,β-saturated carbonyl compound as claimed in claim 1, wherein said method comprises producing an S-form compound chiral at the α-position by the reduction of the carbon-carbon double bond.

9. The method of producing an α-halo-α,β-saturated carbonyl compound as claimed in claim 1, wherein the α-halocarbonyl compound having an α,β-carbon-carbon double bond is a compound represented by the following formula (1):

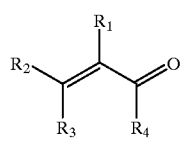

(1)

wherein $R_1$ represents a halogen atom, $R_2$ and $R_3$ each independently represents a hydrogen atom, a halogen atom, a linear or branched aliphatic hydrocarbon group having from 1 to 6 carbon atoms, a linear or branched alkoxy group having from 1 to 6 carbon atoms, a hydroxyl group, a carboxyl group, an aromatic group which may be substituted, or a nitrogen-, oxygen- or sulfur-containing heterocyclic group, and $R_4$ represents a hydroxyl group, a linear or branched alkoxy group having from 1 to 3 carbon atoms or a primary, secondary or tertiary amino group) and the α-halo-α,β-saturated carbonyl compound is a compound represented by the following formula (2):

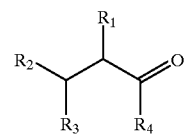

(2)

wherein $R_1$ to $R_4$ have the same meanings as defined above.

10. The method of producing an α-halo-α,β-saturated carbonyl compound as claimed in claim 9, wherein the compound represented by formula (1) is an α-haloacrylic acid and the compound represented by formula (2) is an α-halopropionic acid having an absolute S form configuration.

11. The method of producing an α-halo-α,β-saturated carbonyl compound as claimed in claim 10, wherein the halogen atom is a bromine atom.

12. The method of producing an α-halo-α,β-saturated carbonyl compound as claimed in claim 10, wherein the halogen atom is a chlorine atom.

13. The method of producing an α-halo-α,β-saturated carbonyl compound as claimed in claim 1, wherein the microbial product of a microorganism is a microbial culture, a microbial extract, a microbial cell suspension or a microbial cell fixed to a support.

14. The method of producing an α-halo-α,β-saturated carbonyl compound as claimed in claim 1, wherein the microorganism used varies so as to not decompose the α-halo-α,β-saturated carbonyl compound produced, thereby increasing the amount of the product accumulated.

15. The method of producing an α-halo-α,β-saturated carbonyl compound as claimed in claim 1, wherein the α-halocarbonyl compound having an α,β-carbon-carbon double bond and a compound capable of being oxidized by the microorganism used are present together in the reaction system and thereby the reaction continuing time is prolonged.

16. The method of producing an α-halo-α,β-saturated carbonyl compound as claimed in claim wherein the compound capable of being oxidized by the used is a sugar having from 3 to 6 carbon atoms.

17. The method of producing an α-halo-α,β-saturated carbonyl compound as claimed in claim 15, wherein the compound capable of being oxidized by the microorganism used is an organic acid having from 2 to 4 carbon atoms.

* * * * *